(12) United States Patent
Petrosky

(10) Patent No.: US 8,390,278 B2
(45) Date of Patent: Mar. 5, 2013

(54) EDDY CURRENT INSPECTION PROBE FOR INSPECTING THE INTERIOR OF A TUBULAR MEMBER

(75) Inventor: Lyman J. Petrosky, Latrobe, PA (US)

(73) Assignee: Westinghouse Electric Company LLC, Cranberry Township, PA (US)

( * ) Notice: Subject to any disclaimer, the term of this patent is extended or adjusted under 35 U.S.C. 154(b) by 478 days.

(21) Appl. No.: 12/582,196

(22) Filed: Oct. 20, 2009

(65) Prior Publication Data

US 2011/0089937 A1    Apr. 21, 2011

(51) Int. Cl.
*G01N 27/72* (2006.01)

(52) U.S. Cl. .......... 324/220; 324/221; 324/228; 73/638; 73/865.8

(58) Field of Classification Search .................. None
See application file for complete search history.

(56) References Cited

U.S. PATENT DOCUMENTS

| | | | |
|---|---|---|---|
| 3,593,122 A | 7/1971 | Barton et al. | |
| 4,092,868 A * | 6/1978 | Thompson et al. | 73/638 |
| 4,218,923 A | 8/1980 | Triplett et al. | |
| 4,438,399 A | 3/1984 | Schnabl et al. | |
| 4,668,912 A | 5/1987 | Junker | |
| 4,856,337 A | 8/1989 | Metala et al. | |
| 4,889,679 A | 12/1989 | Snyder et al. | |
| 4,937,524 A * | 6/1990 | Fasnacht et al. | 324/220 |
| 5,062,300 A * | 11/1991 | Vallee | 73/623 |
| 5,105,876 A | 4/1992 | Burack et al. | |
| 5,134,367 A | 7/1992 | Griffith et al. | |
| 5,247,251 A | 9/1993 | Yost et al. | |
| 5,279,168 A | 1/1994 | Timm | |
| 5,355,063 A | 10/1994 | Boone et al. | |
| 5,565,633 A * | 10/1996 | Wernicke | 73/865.8 |
| 5,623,204 A | 4/1997 | Wilkerson | |
| 5,675,084 A | 10/1997 | Goedecke | |
| 5,767,410 A | 6/1998 | Lareau et al. | |
| 5,770,800 A | 6/1998 | Jenkins et al. | |
| 6,429,649 B1 | 8/2002 | Boynton et al. | |
| 6,474,165 B1 | 11/2002 | Harper et al. | |
| 7,405,558 B2 | 7/2008 | Wyatt et al. | |
| 2004/0173116 A1 * | 9/2004 | Ghorbel et al. | 104/138.2 |
| 2004/0261547 A1 | 12/2004 | Russell et al. | |
| 2006/0071663 A1 | 4/2006 | Stanley et al. | |
| 2007/0125175 A1 | 6/2007 | Junker et al. | |
| 2007/0181082 A1 | 8/2007 | Barkich | |
| 2008/0121194 A1 | 5/2008 | Prabhu et al. | |

FOREIGN PATENT DOCUMENTS

EP          1233229 A2    8/2002
WO      WO 9519526       7/1995

* cited by examiner

*Primary Examiner* — Minh N Tang

(57) ABSTRACT

An eddy current probe for inspecting steam generator tubing, that has radially outwardly biased rollers that function to center the probe within the tubing and reduce friction as the probe moves along the interior of the steam generator heat exchanger tube walls. The rollers may include a braking system which controls the drag on the rollers and thus the speed of the probe along the tubing. The direction of travel of the rollers is remotely adjustable to control the inspection pattern and the force of the rollers against the interior surface of the tubing can be remotely controlled.

27 Claims, 5 Drawing Sheets

EDDY CURRENT INSPECTION PROBE FOR INSPECTING THE INTERIOR OF A TUBULAR MEMBER

BACKGROUND OF THE INVENTION

1. Field of the Invention

The present invention relates generally to non-destructive examination of heat exchanger tubing and more particularly to an eddy current probe that exhibits reduced friction and improved centering as it travels within the heat exchanger tubing.

2. Related Art

Steam generators used in nuclear reactor power plants are very large heat exchangers where heat from a primary fluid heated by a nuclear reactor is transferred to a secondary fluid which is converted into steam and used to drive a turbine generator. Steam generators are housed inside a tall, generally cylindrical steel shell. A large number of U-shaped heat exchanger tubes are enclosed in the shell and have their ends inserted in holes formed in a horizontal tube sheet or plate near the bottom of the steel shell. The tubes are used to convey the primary fluid which has been heated in the nuclear reactor. The secondary fluid or feedwater used to generate the steam is introduced into the steam generator in such a manner that the secondary fluid flows around the outside of the heated tubes thereby converting much of the secondary fluid into steam which is allowed to exit the steam generator through an outlet nozzle at the top of the steel shell.

In the past, steam generator tubing in nuclear plants have been exposed to extreme operating conditions and were susceptible to stress corrosion cracking, mechanical wear, wall thinning and pitting. To address this susceptibility, a number of techniques have been developed to inspect steam generator tubing for degradation prior to tubing failure in order to prevent leakage of the primary radioactive coolant into the secondary side which would result in forced outages. Steam generator tubing has been most commonly inspected using a variety of eddy current methods, most involving probes which were inserted into the tubes from the underside of the tube sheet on the primary side of the steam generator. The probes are inserted through a steam generator manway in the lower hemispherical inlet and outlet side of the steam generator below the tube sheet and into the tube sheet whereby the corresponding tubes are mapped by inserting the probes up through the tubes.

One type of eddy current probe that is used for this purpose is the "Bobbin"-type, wherein two coils of copper wire are wound circumferentially around a relatively rigid core to create the test coil. Although widely and relatively successfully used, the relatively rigid Bobbin-type probes are difficult to push through tubes that have bends.

Another type of eddy current probe is a rotating pancake coil probe. The rotating pancake coil probe is ordinarily mounted on a motorized sheath which allows the coil to be simultaneously rotated and translated through the tube thereby developing a helical scan of the tube surface. The pancake eddy current coil axis is normal to the tube inside diameter surface and generally the coil is mounted in an articulating mechanism that allows the coil to follow the inside diameter surface contour, and to maintain a relatively constant coil liftoff.

A third type of eddy current probe employs as many as 40 individual coils that are arranged circumferentially around the probe. Each of the coils provides its own individual output of the opposing inside surface of the heat exchanger tube as the probe is translated axially through the tube.

Generally, each of the foregoing probes needs to be centered as they move through the interior of the heat exchanger tube. Typically, the probes are centered employing compliant pads that extend out radially at spaced circumferential locations around the probe at generally two spaced axial positions. Though highly accurate, the eddy current method of inspecting steam generator tubing is relatively slow and preferably the probes, which are typically pushed along the length of the tubing by a flexible shaft, should be inserted at a constant rate. Side loads developed by the pushing shaft as the probe traverses bends in the tubing and to a lesser extent side loads due to off-center shaft positioning in the straight lengths can adversely impact the centering of the probe or its forward progress.

Accordingly, an improved method of centering the probe is desired that can better navigate bends and resist the effects of side loads from the shaft.

Additionally, an improved method of centering the probe is desired that can reduce resistance to the probe's forward progress as it is pushed through the steam generator tubing.

SUMMARY OF THE INVENTION

These and other objects are achieved by the eddy current inspection probe of this invention which basically includes a housing having an eddy current coil sensor and a centering device supported in a housing with the centering device having a roller arrangement that is designed to ride on the interior walls of the tubing to be inspected and center the eddy current coil within the tubing. Each roller element may be a wheel (disk), roller (cylinder), or ball. Preferably, the roller arrangement has rollers positioned along the housing on a first and second side of the eddy current coil. Preferably, the inspection probe has an axial dimension which extends along the axis of the tube and the rollers are designed to roll in a direction of the axial dimension. In one embodiment, the rollers are designed to roll in either of two orthogonal directions or on a diagonal to the axial dimension. Preferably, the rollers in at least the first or second side of the eddy current coil sensor comprise a set of rollers that are circumferentially spaced around the housing. Desirably, the set of rollers are equally circumferentially spaced around the housing. In another embodiment, the set of rollers comprise at least two rollers and in a preferred arrangement comprise three rollers. Preferably, the rollers are biased radially outward and are at least partially retractable within the housing. Desirably, the rollers can be retracted so they do not have firm contact with the walls of the tubes being inspected.

In another embodiment; at least some of the rollers have an axis of rotation whose orientation can be altered to change the direction of travel of the roller. For at least some applications, the rollers are set at an angle that orients the roller to travel in a helical path. Preferably, the angle is one-half to three degrees offset from the circumferential direction. In still another embodiment, the orientation of the rollers can be altered remotely.

In another embodiment, the roller arrangement of the inspection probe includes a device for measuring speed and/or position of the probe. For example, the device may be a tachometer, encoder or any sensor capable of tracking the roller's movement.

In still another configuration, the roller arrangement of the inspection probe includes a brake for controlling the speed of movement of the probe. In one configuration, the brake includes an electric generator driven by the roller arrangement that further includes a variable load attached to the generator for increasing or decreasing the drag on the roller arrangement. Desirably, the electric generator is configured as a motor generator set that can both drive and brake the roller arrangement.

In still another embodiment, the roller arrangement includes rollers on the first side of the eddy current coil which are circumferentially offset from the rollers on the second side of the eddy current coil.

BRIEF DESCRIPTION OF THE DRAWINGS

A further understanding of the invention can be gained from the following description of the preferred embodiments when read in conjunction with accompanying drawings in which.

DESCRIPTION OF THE PREFERRED EMBODIMENT

Figure 1:
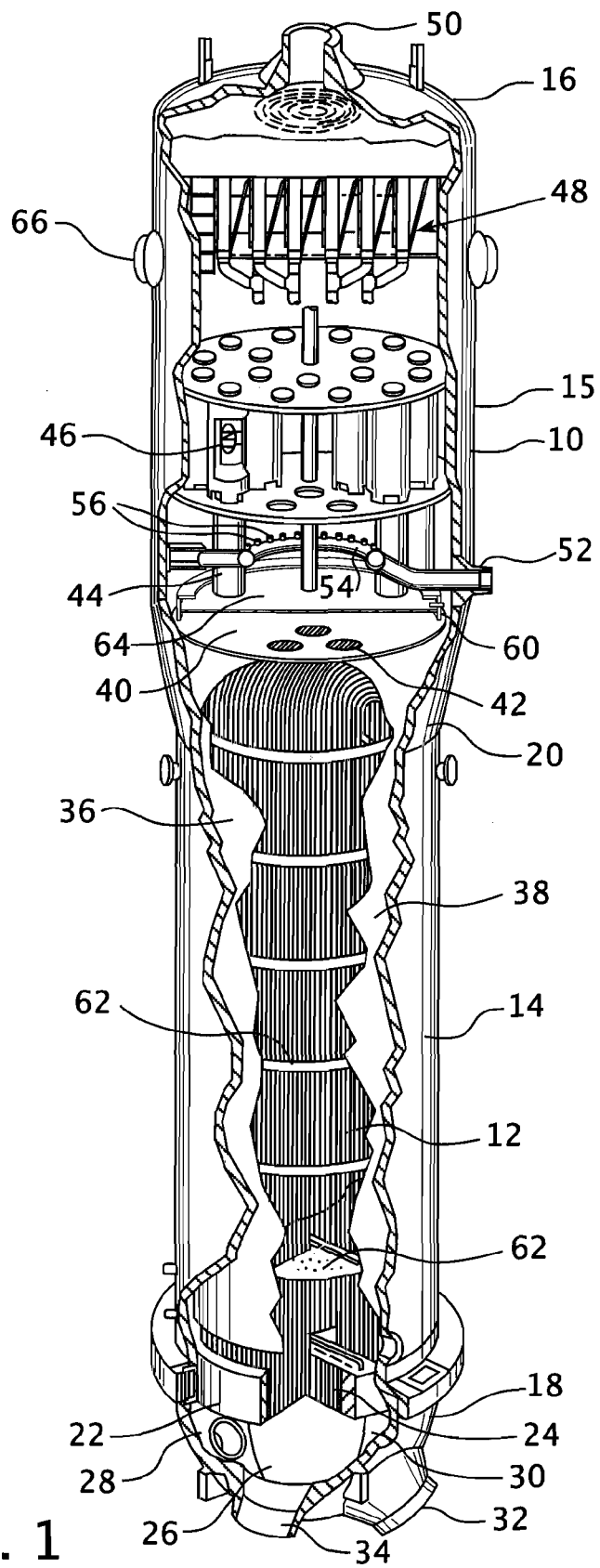
FIG. 1 is a perspective view, partially cut away, of a vertical steam generator for which the eddy current probe of this invention may be applied.

Referring the drawings, FIG. 1 shows a steam or vapor generator 10 that utilizes a plurality of U-shaped tubes which form a tube bundle 12 to provide the heating surface required to transfer heat from a primary fluid traveling within the tubes to vaporize or boil a secondary fluid surrounding the outside of the tubes. The steam generator 10 comprises a vessel having a vertically oriented tubular shell portion 14 and a top enclosure or dished head 16 enclosing the upper end and a generally hemispherical shaped channel head 18 enclosing the lower end. The lower shell portion 14 is smaller in diameter than the upper shell portion 15 and a tube sheet 22 is attached to the channel head 18 and has a plurality of holes 24 disposed therein to receive ends of the U-shaped tubes. A dividing plate 26 is centrally disposed within the channel head 18 to divide the channel head into two compartments 28 and 30, which serve as headers for the tube bundle. Compartment 30 is the primary fluid inlet compartment and has a primary fluid inlet nozzle 32 in fluid communication therewith. Compartment 28 is the primary fluid outlet compartment and has a primary fluid outlet nozzle 34 in fluid communication therewith. Thus, primary fluid, i.e., the reactor coolant, which enters fluid compartment 30 is caused to flow through the tube bundle 12 and out through outlet nozzle 34.

The tube bundle 12 is encircled by a wrapper 36 which forms an annular passage 38 between the wrapper 36 and the shell and cone portions 14 and 20, respectively. The top of the wrapper 36 is covered by a lower deck plate 40 which includes a plurality of openings 42 in fluid communication with a plurality of riser tubes 44. Swirl vanes 46 are disposed within the riser tubes to cause steam flowing therethrough to spin and centrifugally remove some of the moisture entrained within the steam as it flows through the primary centrifugal separator. The water separated from the steam in this primary separator is returned to the top surface of the lower deck plate. After flowing through the primary centrifugal separator, the steam passes through a secondary separator 48 before reaching a steam outlet 50 centrally disposed in the dished head 16.

The feedwater inlet structure of this generator includes a feedwater inlet nozzle 52 having a generally horizontal portion called a feedring 54 and discharge nozzles 56 elevated above the feedring. The feedwater supplied through the feedwater inlet nozzle 52 passes through the feedring 54 and exits through discharge nozzles 56 and mixes with water which was separated from the steam and is being recirculated. The mixture then flows down above the lower deck plate 40 into the annular passage 38. The water then enters the tube bundle at the lower portion of the wrapper 36 and flows along and up the tube bundle where it is heated to generate steam.

The steam generator described above is what is known as a "U-bend" design, because every tube has a single "U" bend midway along its length. A number of other design variations are commonly encountered, such as "square bend" in which the "U" is replaced by two small radius bends (typically 9") and a straight section. There are also steam generators with entirely straight tubes, which feature a plenum at each end of the tube bundle. Regardless of the specific tube pattern and bend arrangement, the invention described herein is applicable to inspect the tubes of such steam generators.

During operation of a steam generator sludge settles around the tubes and loose parts that traverse the tube bundle create an extreme operating environment that makes the tubes in the tube bundle susceptible to stress corrosion cracking, mechanical wear, wall thinning and pitting. To address this susceptibility, a number of techniques have been developed to inspect steam generator tubing for degradation prior to tubing failure in order to prevent forced outages. Steam generator tubing has been most commonly inspected using a variety of eddy current methods, most involving probes which are inserted into the tubes from the underside of the tube sheet 22 on the primary side of the steam generator. The probes are inserted through a steam generator manway in the lower hemispherical inlet and outlet sides of the generator below the tube sheet 22 and into the tube sheet whereby the corresponding tubes are mapped by inserting the probes up through the tubes.

Though highly accurate, the eddy current method of inspecting steam generator tubing is relatively slow and expensive. It is an object of this invention to center the probe while reducing the friction the probe experiences as it moves through the tubes to speed up the inspection process.

Accordingly, this invention provides apparatus that will center the probe within the tubes being inspected and reduce the friction experienced by the probe as it acquires eddy current data in the tubing. The inspection probe travels through the tube being pushed by a flexible shaft. In a broad sense, the innovation adds rollers to the probe to center it and reduce its friction with the tube. While the improved probe can be constructed for use with any size tube, the system has particular advantage for use with small diameter tubing of approximately ⅝ to ⅞ inch outside diameter (1.6-2.2 cm OD), which imposes extreme dimensional limitations and requires excellent centering accuracy.

Current probe heads utilize plastic spring tabs to center the probe in the tube. This arrangement results in less than ideal centering and induces friction at the probe head which greatly impairs the ability of the system to push the probe through tubing with bends. The spring tabs also wear quickly often becoming the life limiting part of the system. It is highly beneficial to eliminate the use of these tabs.

Figure 2:
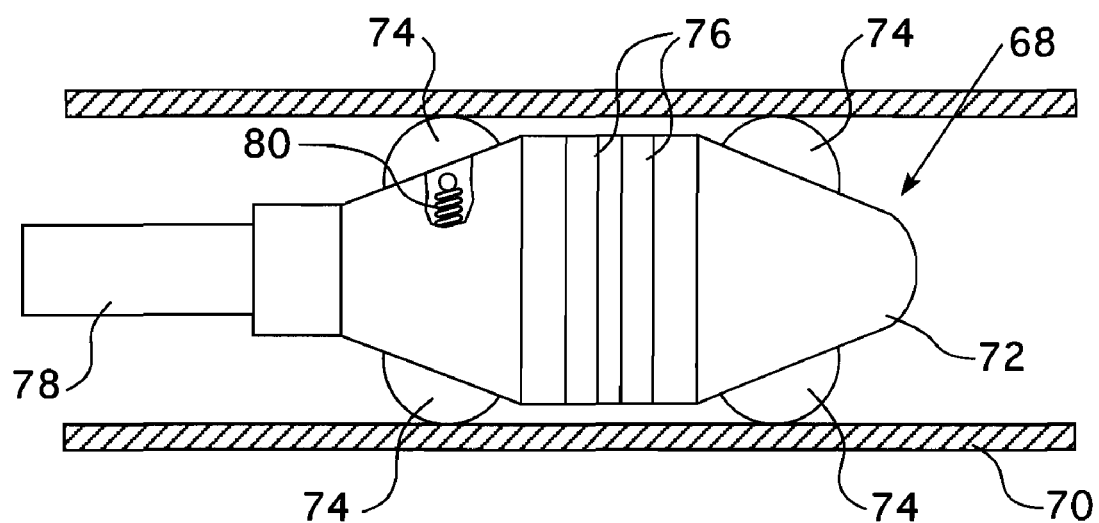
FIG. 2 is a plan view, partially in section of the eddy current probe of this invention inside a steam generator tube to be inspected.

FIG. 2 shows one preferred embodiment of the probe 68 of this invention positioned inside of a steam generator tube 70 and being pushed along by a flexible cable 78. Though the probe head 72 is shown with eddy current Bobbin coils wrapped around a relatively rigid core, the improvement of this invention could be applied as well to other types of eddy current probes such as a rotating pancake coil probe or a coil array probe. The probe head is similar in size and shape to those currently used for tubing inspections, but has, as an added feature, two sets of rollers in the form of wheels 74, one forward and one aft of the eddy current coil 76. The preferred embodiment has three rollers 74 at each axial location that are circumferentially equally spaced around the probe. Preferably, the rollers 74 are spring-biased radially outward against the walls of the tubing, as is figuratively shown by the spring 80. It should be appreciated that the spring-bias action may be achieved by the use of any compliant mechanism. It should also be appreciated though that the wheel shafts can be provided with an electro-mechanical actuator, such as a solenoid, to radially retract the rollers to control or eliminate the pressure of the rollers 74 on the walls of the tubing 70.

Figure 3:
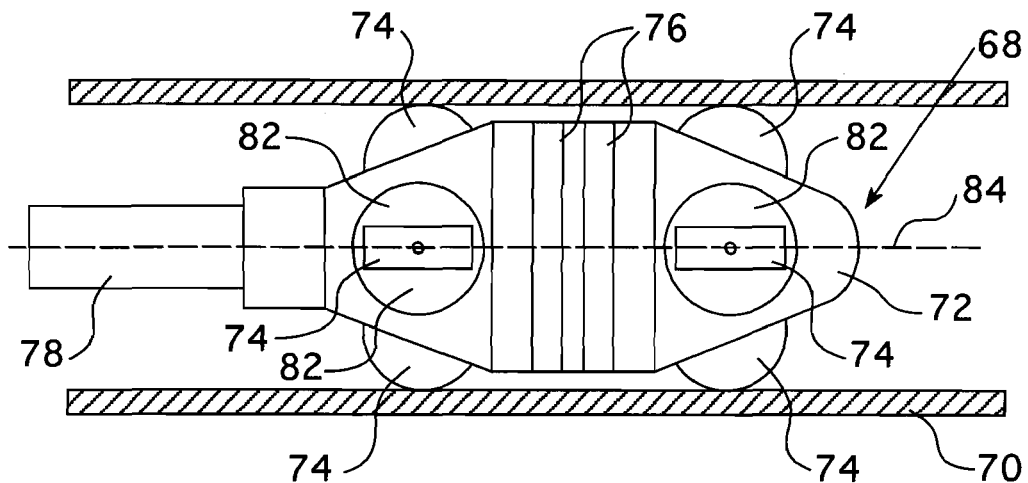
FIG. 3 is the plan view of FIG. 2 with the probe of this invention including rollers whose direction can be adjusted.

FIG. 3 shows a slight modification to the probe 68 that was previously illustrated in FIG. 2. The rollers 74 shown in FIG. 3 are mounted on a turntable 82 so they can be adjusted to point in any direction to enable the probe to move either axially in the direction of the tube axis 84 or alternately, to be turned on a diagonal to the axis 84 to spiral through the pipe 70 or to be turned in an orthogonal direction to the axis 84 to rotate in place. Preferably, the turntables 82 rotate together so that the rollers are all pointing in the same direction and desirably the turntables 82 can be rotated remotely from outside of the steam generator so that the tube scans can be adjusted while the inspection is in process.

Figure 4A:
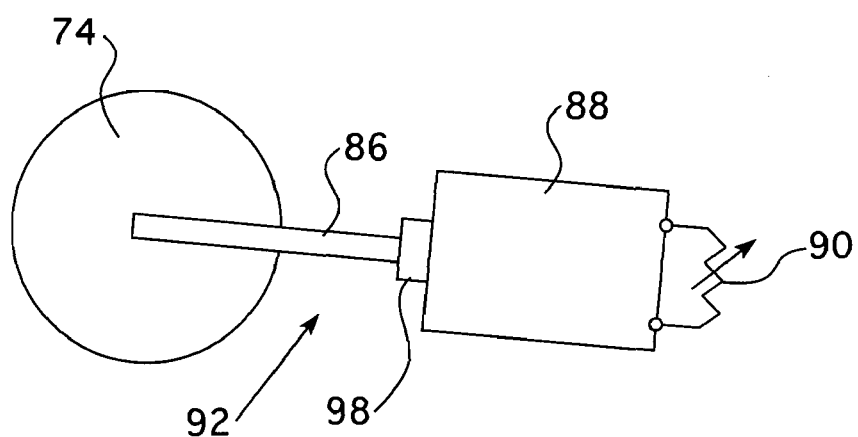
FIG. 4A is a schematic diagram showing one roller of the probe illustrated in FIGS. 2 and 3 connected to the motor generator braking set of this invention.

FIG. 4A shows a braking system 92 which can be employed with the rollers 74. The braking system 92 is attached to the rollers 74 through a drive shaft 86 that couples the rollers 74 to an electric generator 88. The drive shaft 86 turns the armature of the electric generator 88 which in turn produces an electric current that is conveyed through an electronically variable load such as the variable resistor 90 that can be adjusted from outside the steam generator. Increasing the load increases the drag on the roller 74. The cabling to control the variable load 90 as well as the sensor coil cabling is conducted through the flexible shaft 78 to the exterior of the generator to a control station, not shown, which records the eddy current coils output as well as controls the braking action of the generator 88 by adjusting the variable load 90. Preferably, the electric generator 88 is a motor generator set that can drive the drive roller 74. Alternately, the probe head 72 can be pushed through the tubing 70 with compressed air.

Figure 4B:
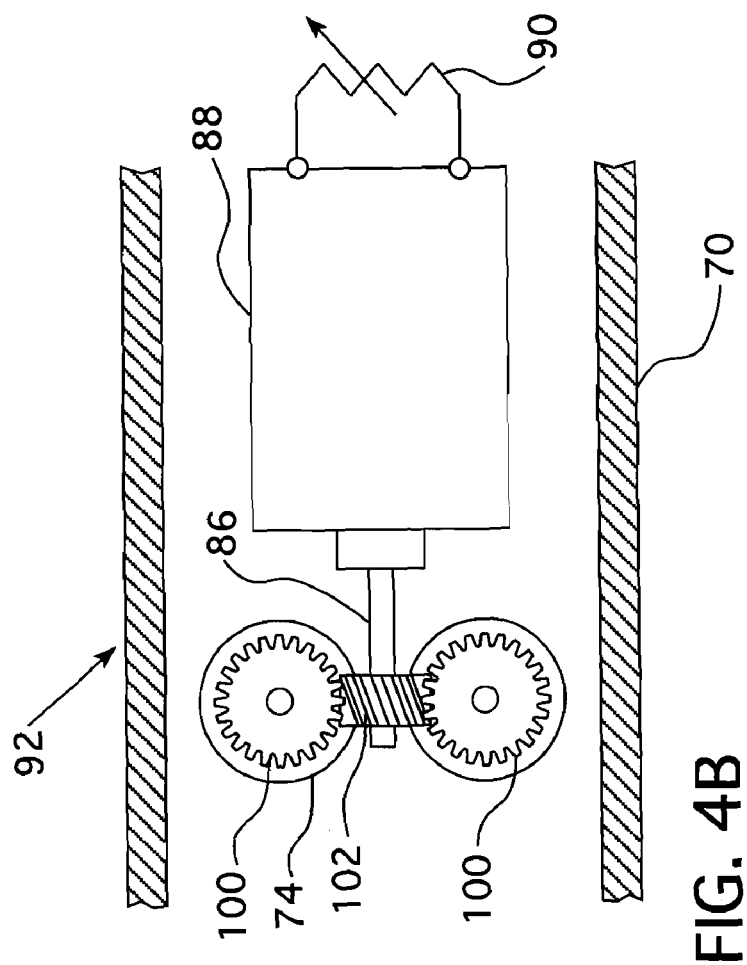
FIG. 4B is a side sectional view of a heat exchanger tube with the roller drive of FIG. 4A schematically shown inside.
Figure 4C:
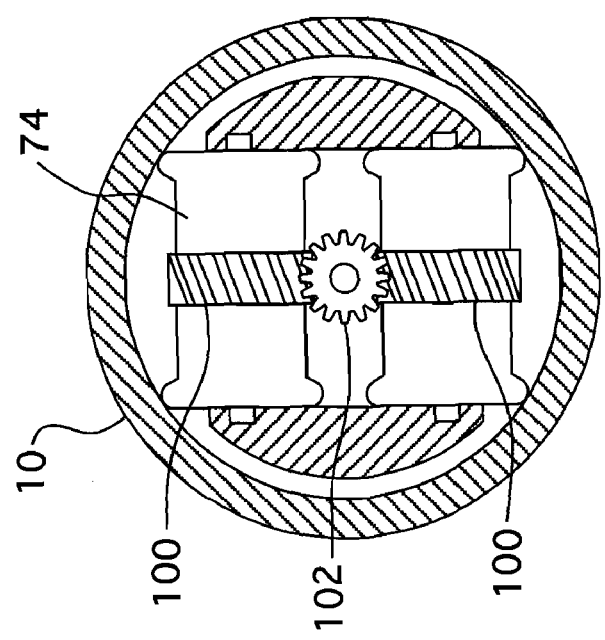
FIG. 4C is an end view of the heat exchanger tube shown in FIG. 4B.

FIG. 4B shows more detail of one embodiment of the coupling between the rollers 74 and the motor/generator 88. Each of the drive rollers 74 is provided with a helical gear 100 that engages a helical gear on the motor/generator shaft 86. The motor/generator may either drive the rollers or the rollers may drive the motor generator, which will create drag and may generate power.

Figure 5:
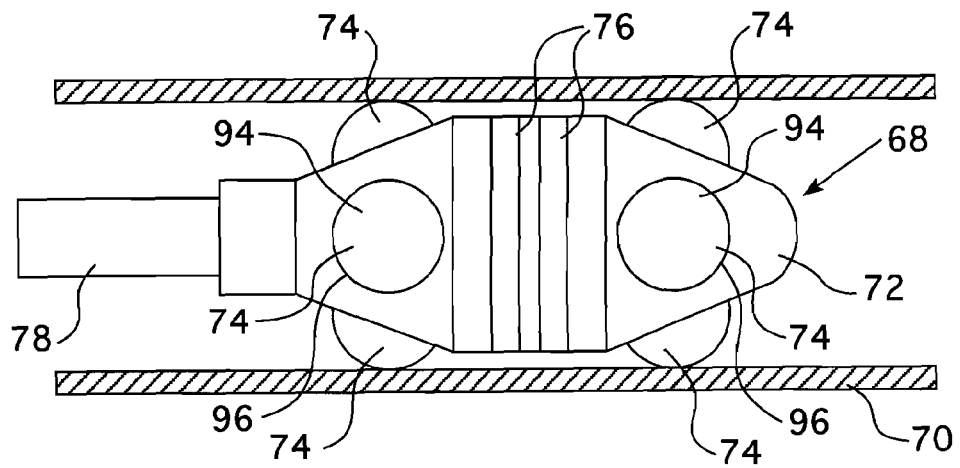
FIG. 5 is a plan view of the probe of this invention shown in FIGS. 2 and 3 with the rollers configured as a ball that rides in a socket which enables the rollers to move in any direction.

FIG. 5 shows another embodiment in which the rollers 74 are formed from balls 94 that ride in ball sockets 96. The balls 94 take the place of the turntables 82 previously described with regard to FIG. 3, but similarly enable the probe head 82 to move in any direction along the interior surface of the pipe 70.

Figure 6:
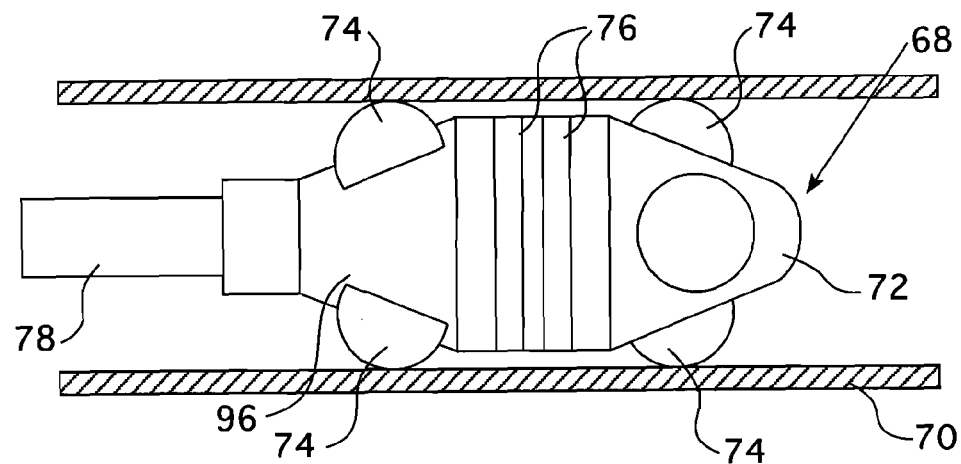
FIG. 6 is the plan view shown in FIGS. 2, 3 and 5 with the rollers on one side of the eddy current coil circumferentially offset from the rollers on the other side of the eddy current coil.

FIG. 6 shows another alternate embodiment to that shown in FIG. 5 wherein the rollers 74 in each roller set on either side of the eddy current coil 76 are circumferentially equally spaced, with one set of rollers circumferentially offset from the other set of rollers.

The improved probe as just described will increase the life of the probe head 72 and reduce friction as the probe extends along the interior surface of the pipe 70 to help speed up the inspection process. In one embodiment, the rollers are directed at an angle perpendicular to the tube axis of between one-half and three degrees and preferably at an angle of one degree to enable the probe to helically traverse the interior surface of the tube under inspection. In still another embodiment, the rollers are provided with a device for measuring the speed and/or position of the probe 68, such as shown by reference character 98 in FIG. 4A. For example, the device 98 can be a tachometer and/or an encoder.

While specific embodiments of the invention have been described in detail, it will be appreciated by those skilled in the art that various modifications and alternatives to those details could be developed in light of the overall teachings of the disclosure. Accordingly, the particular embodiments disclosed are meant to be illustrative only and not limiting as to the scope of the invention which is to be given the breath of the appended claims and any and all equivalents thereof.

What is claimed is:

1. An eddy current inspection probe for the nondestructive examination a wall of the interior of a tubular object having an axial dimension, comprising:
   a housing;
   an eddy current coil supported by the housing; and
   a roller arrangement including a plurality of rollers supported by the housing and biased against the wall of the interior of the tubular object; and
   a brake for imparting an adjustable drag force on at least one of the rollers to vary the speed of the at least one of the rollers as the housing moves through the interior of the tubular object, wherein the brake includes an electric generator driven by the roller arrangement including a variable load attached to the generator for increasing or decreasing the drag on the roller arrangement.

2. The eddy current inspection probe of claim 1 wherein the roller arrangement comprises rollers positioned along the housing on a first and second side of the eddy current coil.

3. The eddy current inspection probe of claim 2 wherein the inspection probe has an axial dimension and the rollers are designed to roll in a direction of the axial dimension.

4. The eddy current inspection probe of claim 3 wherein the rollers are designed to roll in at least two orthogonal directions.

5. The eddy current inspection probe of claim 2 wherein the inspection probe has an axial dimension and the rollers are designed to roll in a direction at a diagonal to the axial dimension.

6. The eddy current inspection probe of claim 2 wherein the rollers positioned on at least the first or second side of the eddy current coil comprise a set of rollers that are circumferentially spaced around the housing.

7. The eddy current inspection probe of claim 6 wherein the set of rollers are equally circumferentially spaced around the housing.

8. The eddy current inspection probe of claim 6 wherein the set of rollers comprises two rollers.

9. The eddy current inspection probe of claim 6 wherein the set of rollers comprises three rollers.

10. The eddy current inspection probe of claim 2 wherein the rollers positioned on the first and second sides of the eddy current coil comprise a set of rollers that are circumferentially spaced around the housing.

11. The eddy current inspection probe of claim 2 wherein at least some of the rollers are configured to be retracted so they do not have firm contact with the tubular object.

12. The eddy current inspection probe of claim 2 wherein at least some of the rollers have an axis of rotation whose orientation is configured to be altered to change the direction of travel of the roller over at least ninety degrees.

13. The eddy current inspection probe of claim 12 wherein the probe has an axial dimension which coincides with an axial dimension of the tubular object and the at least some of the rollers are set at an angle that orients the roller to travel in a helical path.

14. The eddy current probe of claim 13 wherein the angle is 1 to 3 degrees off the axial dimension.

15. The eddy current inspection probe of claim 12 wherein the orientation of the axis of rotation is configured to be altered remotely.

16. The eddy current inspection probe of claim 1 wherein the roller arrangement includes a device for measuring speed and/or position of the probe.

17. The eddy current inspection probe of claim 16 wherein the device is selected from the group of a tachometer and encoder.

18. The eddy current inspection probe of claim 1 wherein the electric generator further includes a motor generator set that is configured to both drive and brake the roller arrangement.

19. The eddy current inspection probe of claim 1 wherein the generator has a shaft which is directly connected to at least one roller on the roller arrangement through a helical gear assembly.

20. The eddy current inspection probe of claim 19 wherein the helical gear assembly comprises a helical gear on the roller that mates with a helical gear on the generator shaft.

21. The eddy current inspection probe of claim 1 wherein the roller arrangement comprise rollers on a first side of the eddy current coil circumferentially offset from the rollers on a second side of the eddy current coil.

22. An eddy current inspection probe for the nondestructive examination of a wall of the interior of a tubular object having an axial dimension, comprising:
 a housing;
 an eddy current coil supported by the housing; and
 a roller arrangement including a plurality of rollers supported by the housing and biased against the wall of the interior of the tubular object; and
 wherein at least some of the rollers have an axis of rotation whose orientation is configured to be altered to change the direction of travel of the at least some of the rollers over at least ninety degrees.

23. The eddy current inspection probe of claim 22 wherein the probe has an axial dimension which coincides with an axial dimension of the tubular object and the at least some of the rollers are set at an angle that orients the roller to travel in a helical path.

24. The eddy current probe of claim 23 wherein the angle is 1 to 3 degrees off the axial dimension.

25. The eddy current inspection probe of claim 22 wherein the orientation of the axis of rotation is configured to be altered remotely.

26. An eddy current inspection probe for the nondestructive examination of a wall of the interior of a tubular object having an axial dimension, comprising:
 a housing;
 an eddy current coil supported by the housing; and
 a roller arrangement including a plurality of rollers supported by the housing and biased against the wall of the interior of the tubular object; and
 a brake for imparting a variable drag force on at least one of the rollers to control the speed of the at least one of the rollers as the housing moves through the interior of the tubular object without imparting a drive force on the at least one of the rollers.

27. The eddy current inspection probe of claim 26 wherein the drag force is varied remotely.

* * * * *